United States Patent [19]

Young, II

[11] 4,136,961

[45] Jan. 30, 1979

[54] METHOD AND APPARATUS FOR DETECTION OF INCLUSIONS IN GLASS ARTICLE OR THE LIKE

[75] Inventor: Roy V. Young, II, Painted Post, N.Y.

[73] Assignee: Corning Glass Works, Corning, N.Y.

[21] Appl. No.: 812,340

[22] Filed: Jul. 1, 1977

[51] Int. Cl.² .............................................. G01N 21/32
[52] U.S. Cl. ................................... 356/239; 250/224; 356/398
[58] Field of Search ................. 356/30, 167, 239, 240; 250/224

[56] References Cited

U.S. PATENT DOCUMENTS

| 3,586,444 | 6/1971 | Sproul et al. | 356/239 |
| 3,639,067 | 2/1972 | Stephens | 356/240 |
| 3,989,380 | 11/1976 | Spitz | 356/240 |

*Primary Examiner*—John K. Corbin
*Assistant Examiner*—R. A. Rosenberger
*Attorney, Agent, or Firm*—Walter S. Zebrowski; Frederick W. Powers, III

[57] ABSTRACT

An automatic system for scanning a generally cylindrical member with a thin beam of light. Detectors are provided for sensing interruption or scattering of the light beam by inclusions within the member. When an inclusion is detected transverse scanning stops and the beam is fixed along a chord of the cylinder. The cylinder is then rotated to cause the inclusion to intercept the chordal beam, and the information thus generated is used to identify the type and position of inclusions within the blank.

13 Claims, 5 Drawing Figures

METHOD AND APPARATUS FOR DETECTION OF INCLUSIONS IN GLASS ARTICLE OR THE LIKE

BACKGROUND OF THE INVENTION

The present invention relates to optical inspection means, and more particularly to an automated system for detecting inclusions in generally cylindrical blanks of material.

Although many aspects of the production of glass and similar materials have been highly automated, certain aspects of quality control procedures have remained substantially subjective. In particular, the method commonly used for detecting inclusions in glass has taken two forms. In order to detect inclusions in in-process glass material a small portion of the molten material is typically drawn off and molded into an appropriate form termed a glass "patty". The patty is then inspected by a qualified individual using optical aids such as magnifying glasses and the like. The type, number and size of inclusions are then taken to be representative of the batch of glass in accordance with usual sampling procedures. If the nature of the inclusions is such as to suggest that a batch of glass is below some predetermined standards the batch may be reinspected, reprocessed, or scrapped.

Another technique is known and frequently used for inspecting cylindrical glass blanks, particularly blanks to be drawn into elongate optical waveguides. As is understood by those skilled in the art, due to the extremely small size of optical waveguides and to the character of the signals which they are called upon to transmit very small inclusions in a blank may render it useless. At the same time, certain types of inclusions may be acceptable for use in a waveguide blank depending upon their density, i.e., their closeness to one another. In order to inspect such blanks, they are conventionally immersed in a liquid having an index of refraction substantially the same as the glass. The blanks are then visually inspected using conventional apparatus such as magnifying glasses and the like.

It will be apparent that such inspection procedures leave much to be desired. In particular it is extremely difficult for an individual to count the number of small inclusions which are close to one another, or to accurately characterize the spatial distribution of a group of inclusions. Since the inclusions lie within the volume of the glass member under inspection it is impossible to measure their position directly.

Still further, it is often important that the type of inclusion be recognized. Inclusions may generally be classified in two groups: solid inclusions, which are formed by bits of unmelted or foreign material; and void inclusions, commonly formed by bubbles of gas. Solid inclusions generally are formed by minute impurities in the starting materials which are fused to form a glass; bits of refractory material from the walls of the vessel in which the glass is prepared; or bits of platinum from the walls of conduits through which the glass stream flows. In some cases, the solid inclusions are opaque; in others, they are clear. It is then apparent that differentiating a clear inclusion from a void inclusion, or gas bubble, can present difficulties in visual inspection. Nonetheless it is increasingly important that such inclusions be counted, properly characterized, and their spatial distribution established. Still further, for the case of materials which are opaque to visible light the detection of various types of inclusions has heretofore been practically impossible to achieve on a commercial basis. It will therefore be understood that it would be highly desirable to improve the integrity of inspection procedures beyond their present levels.

It is therefore an object of the present invention to provide means for automatically inspecting a generally cylindrical blank of material for inclusions.

It is another object of the invention to provide means for automatically scanning a blank of material which is transparent to electromagnetic radiation with a beam of such radiation for detecting inclusions.

Another object is to provide a method of scanning a generally cylindrical blank of glass or the like.

Still another object is to provide a system for defining the location of individual inclusions within a cylindrical blank.

Another object is to provide a system which automatically scans a blank of material with a beam of electromagnetic radiation and determines the number of inclusions detected and their relative position.

SUMMARY OF THE INVENTION

Briefly stated, in accordance with one aspect of the invention the foregoing objects are achieved by providing a beam of electromagnetic radiation, and means for rotating a generally cylindrical blank in the beam to cause the beam to traverse chords of the blank. Sensing means are provided for determining the relative position of the radiation beam and the blank, and photosensors provided adjacent the blank to detect both discontinuities in the beam, denoting the presence of solid inclusions; and scattering of the beam, caused by void inclusions. A signal processing system combines signals derived from the various sensing means to provide an indication of the number and position of the detected inclusions.

BRIEF DESCRIPTION OF THE DRAWINGS

While the specification concludes with claims particularly pointing out and distinctly claiming the subject matter which is regarded as the invention, it is believed that the invention will be better understood from the following description of a preferred embodiment taken in conjunction with the accompanying drawings in which:

DESCRIPTION OF A PREFERRED EMBODIMENT

Figure 1:
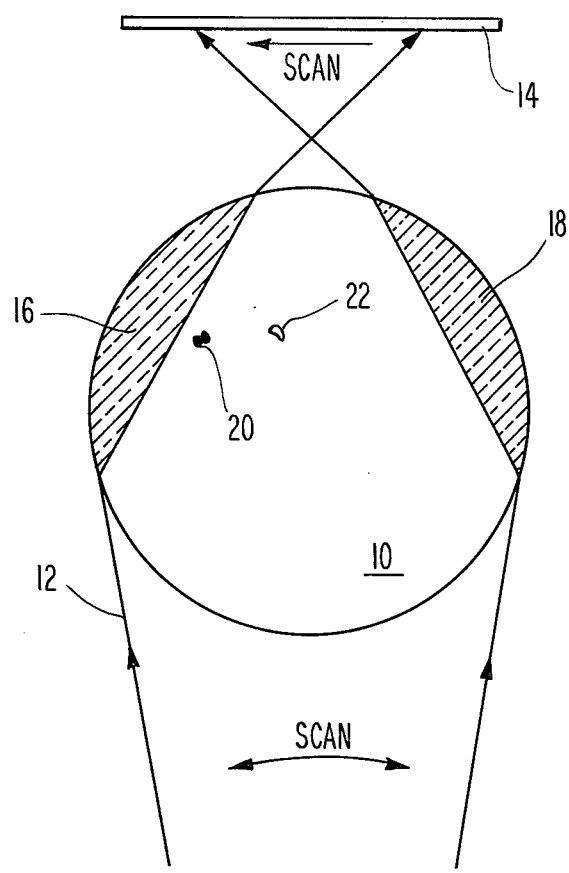
FIG. 1 illustrates the transverse scanning of a material blank.

FIG. 1 represents a generally cylindrical blank 10 of a material which is transparent to a scanning beam of electromagnetic radiation. Present commercial applications of the invention are in the field of glass making, and accordingly for purposes of description inspected blanks will be considered to be formed of transparent glass. Accordingly, the beam of electromagnetic radiation used for inspection purposes may be visible light and will be so described. In the Figure blank 10 is stationary, and a light beam 12 is scanned across the blank. Due to well-known principles of geometrical objects when the beam begins to intercept the blank at an outermost edge it is refracted inwardly, passing through the blank and exiting after a second refraction. An inversion effect takes place whereby the leftwardmost or starting position of the beam impinges at the rightwardmost extremity of the scanned field of a photosensor 14. The photosensor, which may be silicon or any other appropriate type, is depicted as planar although those skilled in the art will recognize that other configurations may be adopted. Accordingly, the specific configuration or type of sensors used is not considered to be of consequence with respect to the practice of the invention.

As the illustrated beam encounters the leftward side of blank 10 it is initially reflected from the surface thereof. As the angle of incidence increases it penetrates the blank, and is refracted as shown. Due to the geometries involved there is a "dead zone" 16 which is not traversed by the beam; similarly, as the beam completes its scan a complementary dead zone 18 occurs at the opposite side of the blank. As the beam 12 scans across the blank, the refracted beam which exits from the opposite side of the blank scans across detector 14 in the reverse direction, as shown.

Depicted within blank 10 are a pair of inclusions 20 and 22. Inclusion 20 is represented as a solid intrusion, while inclusion 22 is a void or gaseous inclusion. Such inclusions often arise in the process of forming glass and other fused materials, and are attributable to impurities in the vessels used to prepare the material or to aberrations in the forming process whereby bubbles of air or the like are introduced into a blank.

Inasmuch as scanning beam 12 traverses all of the area of blank 10 except for dead zones 16 and 18, it will be understood that the beam necessarily intercepts the inclusions. The present inventor has found that the effect of inclusions upon a scanning beam varies markedly with the type of inclusion; and that appropriate sensing means can be provided to not only identify the presence of an inclusion, but to differentiate between solid and void inclusions.

Figure 2:
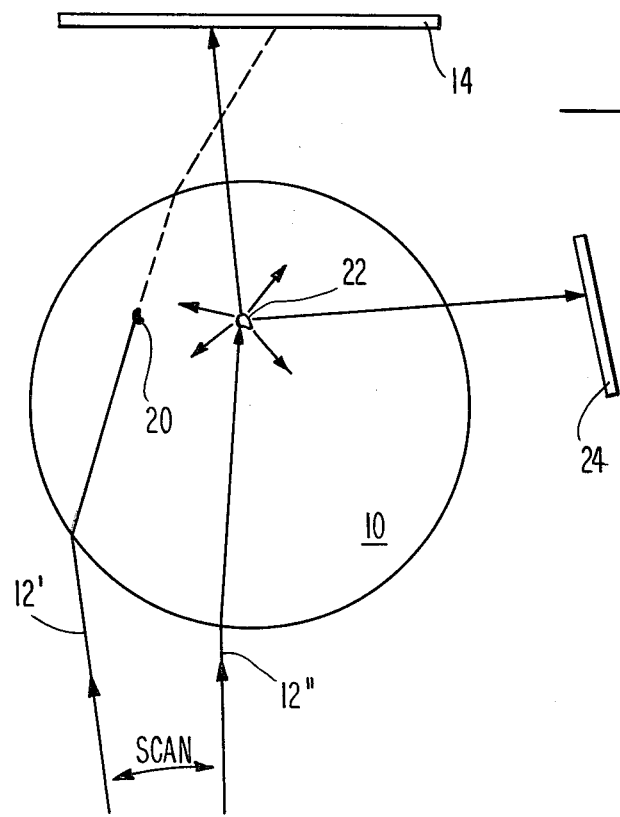
FIG. 2 depicts the effects of inclusions upon a scanning beam.

Turning now to FIG. 2, beam 12' has scanned to a position wherein it is intercepted by solid inclusion 20. A dotted line represents the normal path of beam 12' in the absence of the inclusion, whereby the beam would ordinarily strike sensor 14. Assuming that the beam had previously been impinging upon the sensor, a substantially continuous signal will have been produced by the latter. When the beam encounters a solid inclusion which is opaque the beam is temporarily blocked and the electrical output of the sensor drops suddenly. A discontinuity or "spike" thus occurs in the electrical output of sensor 14.

It has been found that transparent, solid inclusions produce substantially the same response as opaque ones. This is attributable to the fact that the index of refraction of the transparent inclusions is substantially different from the surrounding glass, effecting a substantially scattering and/or bending of the light beam. While the scattering which is produced is preferential, i.e., directed toward sensor 14, the intensity of light striking the sensor is still diminished markedly and accordingly the presence of the inclusion can be detected.

Consider now beam 12", representing the position of the inspection beam after it has moved closer to the center of blank 10. Beam 12" now intercepts void inclusion 22 with the result that the light is scattered in substantially a 360° pattern. Accordingly, a portion of the light falls upon first sensor 14. Although there is a reduction in the level of the signal outputted by the latter, it is not ordinarily substantial enough to allow the presence of the void inclusion to be detected with a high degree of integrity. The present inventor has found that by providing a second detector 24 substantially displaced from the normal path of the scanned beam after it exits from the blank, light which is scattered from void inclusions can readily be detected. Accordingly, the production of an electrical signal by second sensor 24 is taken to indicate that a scanned beam has encountered a void inclusion in the blank.

While the approach thus far described is effective to identify the presence of individual inclusions and further to identify the type of inclusion, i.e., whether solid or void, there is insufficient information generated to allow the positions of the various inclusions to be determined. Additional steps are then necessary in order to obtain an indication of the position of each inclusion.

Figure 3:
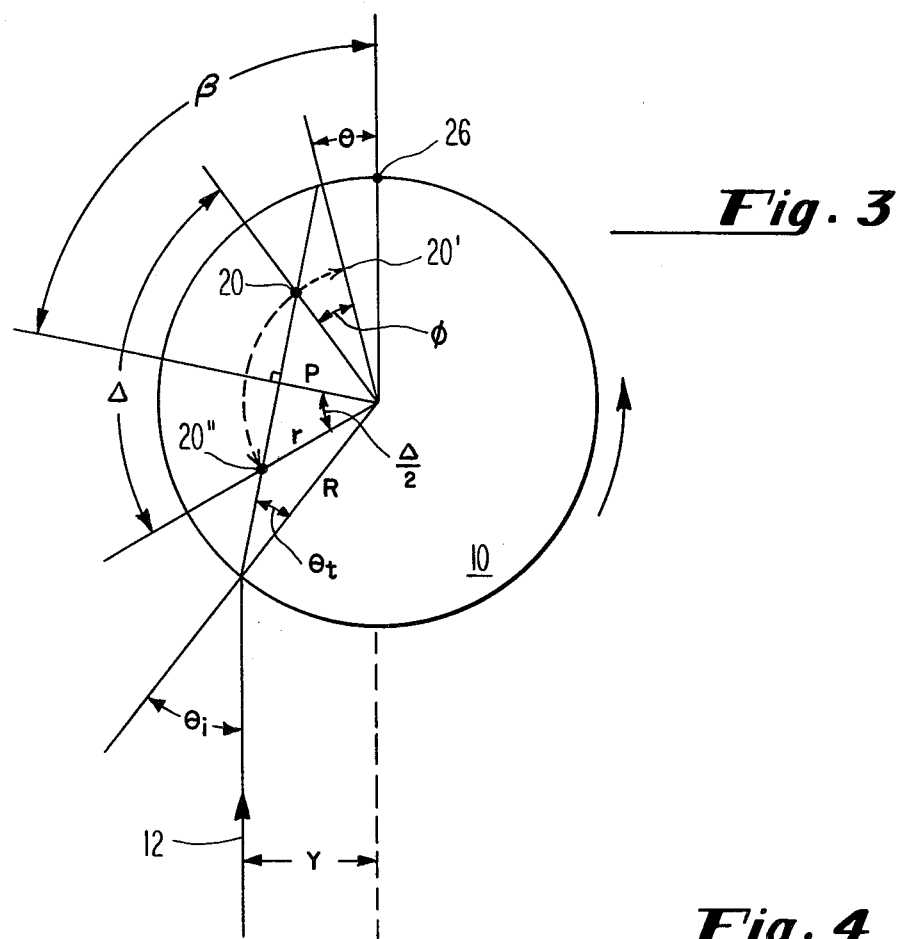
FIG. 3 illustrates certain geometrical relationships made use of by the present invention.

FIG. 3 illustrates the geometric relationships involved in making such a determination. The inspection beam 12 is translated a predetermined distance Y, so that it impinges upon a specific point on the periphery of blank 10. While the point selected is not critical, it is necessary that the point not be directly in a line between the geometrical center of the blank and the light source. Accordingly, light beam 12 strikes the side of blank 10 at some angle of incidence $\theta_i$ and is refracted so that it traverses a chord of the generally cylindrical blank. The angle of transmission $\theta_t$ is determined by the relative index of refraction n of the material from which the blank is made. The angles $\theta_i$ and $\theta_t$ are related in accordance with the wellknown relationship $$\sin \theta_i = n \sin \theta_t \qquad (1)$$

The perpendicular distance between the center of the chord and the geometric center of blank 10 is represented as dimension P and the radius of blank 10 is designated R. A reference point 26 is identified upon the blank, or upon a fixture which holds the blank. Blank 10 is then rotated about its geometric center in a counterclockwise direction until beam 12 is intercepted by an inclusion. In the present illustration blank 10 is rotated some angle $\phi$. Accordingly, every point within the body of blank 10 rotates by the same angle $\phi$ including solid inclusion 20. After rotating through $\phi$ from its original position 20' the inclusion intercepts beam 12. Inasmuch as the inclusion is a solid one the interception of the inspection beam is sensed by sensor 14. It should be understood, however, that should the inclusion be void the scattered light detector 24 will signal the interception of beam 12 at precisely the same point depicted in the Figure.

Rotation of blank 10 continues at least until the inclusion intercepts the inspection beam a second time, herein depicted at point 20". From basic geometry it is apparent that the radii V from the center of rotation of blank 10 to the points at which the chordal inspection beam is intercepted are precisely the same. Further, the angle between a radius r and the perpendicular P between the chordal locus of the inspection beam and the axis of rotation of the blank is just one-half the total included angle between positions 20' and 20". This included angle is denominated $\Delta$. Finally, some fixed angle $\beta$ exists between perpendicular P and an arbitrary starting position indicated by mark 26.

Given the foregoing information, the precise location of void 20 with respect to index point 26 in the scanned plane can be determined. Since the included angle $\Delta$ is known, the angle between perpendicular P and unknown radius r is defined as $\Delta/2$. Accordingly, the radius r can be calculated according to the equation $$r = \frac{P}{\cos \frac{\Delta}{2}} \quad (2)$$

For calibration purposes it is of interest to establish the relationship between the radius r and the angle of incidence $\theta_i$. Since the angle of incidence is also related to the lateral displacement Y of the incident beam by displacing the beam a known distance the dimension of perpendicular P can be ascertained, and the radius r easily calculated.

From FIG. 3 it will be seen that $$\sin \theta_t = \frac{P}{R} \quad (3)$$

or $$P = R \sin \theta_t \quad (4)$$

but $$\sin \theta_t = \sin \frac{\theta_i}{n} \quad (5)$$

so that $$P = R \sin \frac{\theta_i}{n} \quad (6)$$

Substituting in Equation (2), we see that $$r = \frac{\frac{R}{n} \sin \theta_i}{\cos \frac{\Delta}{2}} \quad (7)$$

If desired, the angular relationship $\theta$ between inclusion 20 and index point 26 can be established. Since the total included angle $\beta$ between the initial position of index point 26 and perpendicular P is known, if the quantities $\Delta/2$ and $\phi$ are subtracted from the total angle $\beta$ the remainder will be the quantity $\theta$, or $$\theta = \beta - (\Delta/2 + \phi)$$

Accordingly, the precise position of inclusion 20 within blank 10 can be designated using a polar coordinate system.

Only a single transverse plane of blank 12 is depicted. The length of blank 10 is not of consequence, except of course that the longer the blank the more transverse planes which can be defined through it, and accordingly a correspondingly larger number of scans will be needed. However, by identifying the position of scanning beam 12 with respect to the longitudinal axis of blank 10, the position of inclusion 20 along the blank axis can readily be determined. The axial position may be denominated x, so that a complete set of cylindrical coordinates r, $\theta$, and x may be defined.

Figure 4:
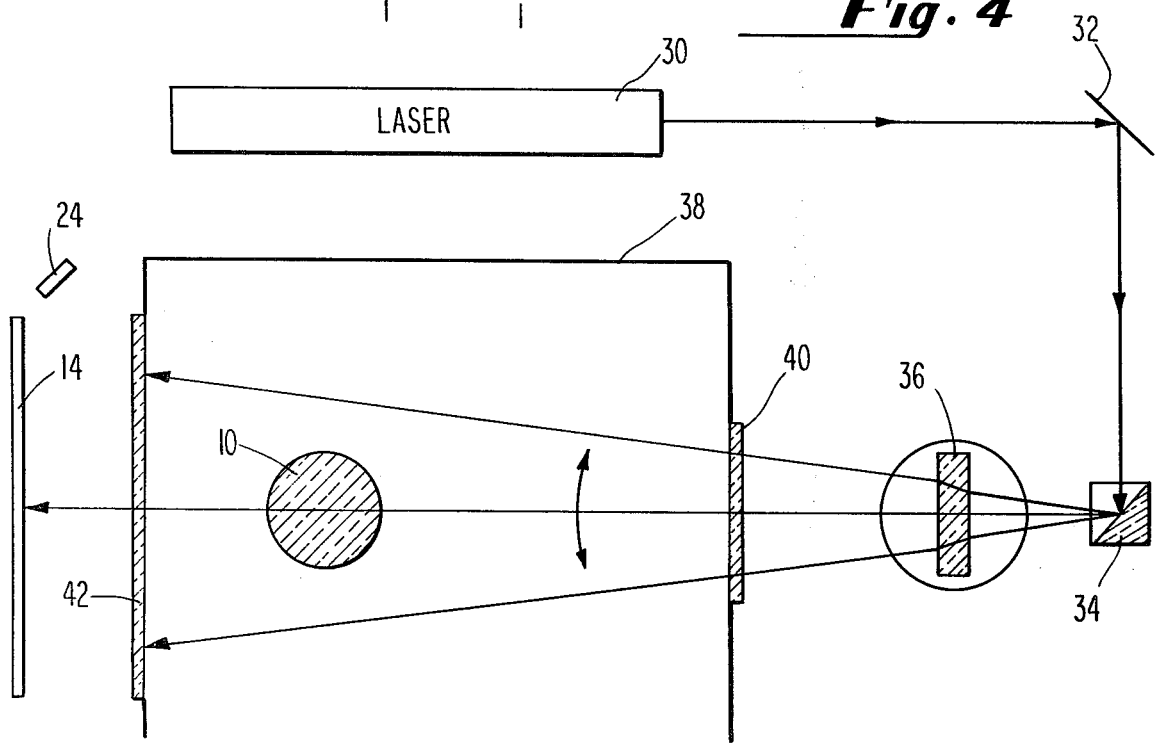
FIG. 4 is an optical system arranged in accordance with the invention.

Turning now to FIG. 4 there appears one system for accomplishing both a transverse scanning of a blank by a laser beam, and for causing the beam to impinge on the blank some distance Y from a radial center line. The source of a beam of electromagnetic energy, preferably a laser 30, is disposed in a convenient position and its beam deflected by means of one or more mirrors 32 to a scanner including a prism 34. The beam is then reflected from the scanner and it traverses a transparent prism 36 having parallel front and rear faces, hereinafter referred to as a parallelogram prism. An enclosure 38, which may be a simple sheet metal housing, extends over blank 10 and supports first and second windows 40, 42. In a preferred embodiment the windows are coated to diminish reflection, and may further constitute appropriate interference filters. The beam exits from the rear window 42 and impinges upon detectors 14 and 24.

In order to scan blank 10, parallelogram 36 is disposed so that its faces are normal to the path of the laser beam. The scanner prism 34 is oscillated to cause the laser beam to sweep back and forth across the blank. Due to the refraction effect of the parallelogram prism material there will be some deflection of the beam; however this deflection is considered immaterial for present purposes.

When the inspecting beam encounters a solid inclusion, the diminishing signal from detector 14 will signal its presence. Similarly, when a void inclusion is detected, detector 24 will produce an appropriate output. In the absence of such an output, blank 10 will be moved axially through the scanning field in small increments, for instance 0.005 inches. When an inclusion is detected translation of the blank ceases and scanner prism 34 is caused to adopt a central position. Parallelogram prism 36 is then rotated slightly so that it intercepts the inspection beam at a small angle. Due to the refraction of the parallelogram, as is well understood by those skilled in the art, the inspection beam will be displaced some distance Y from its original path and continue toward blank 10 along a locus which is parallel to its original, undeflected path. The inspection beam will then be incident upon the surface of the blank at some angle of incidence $\theta_i$ as depicted in FIG. 3 and the blank 10 can be rotated to determine the specific location of the inclusion which has been detected.

Figure 5:
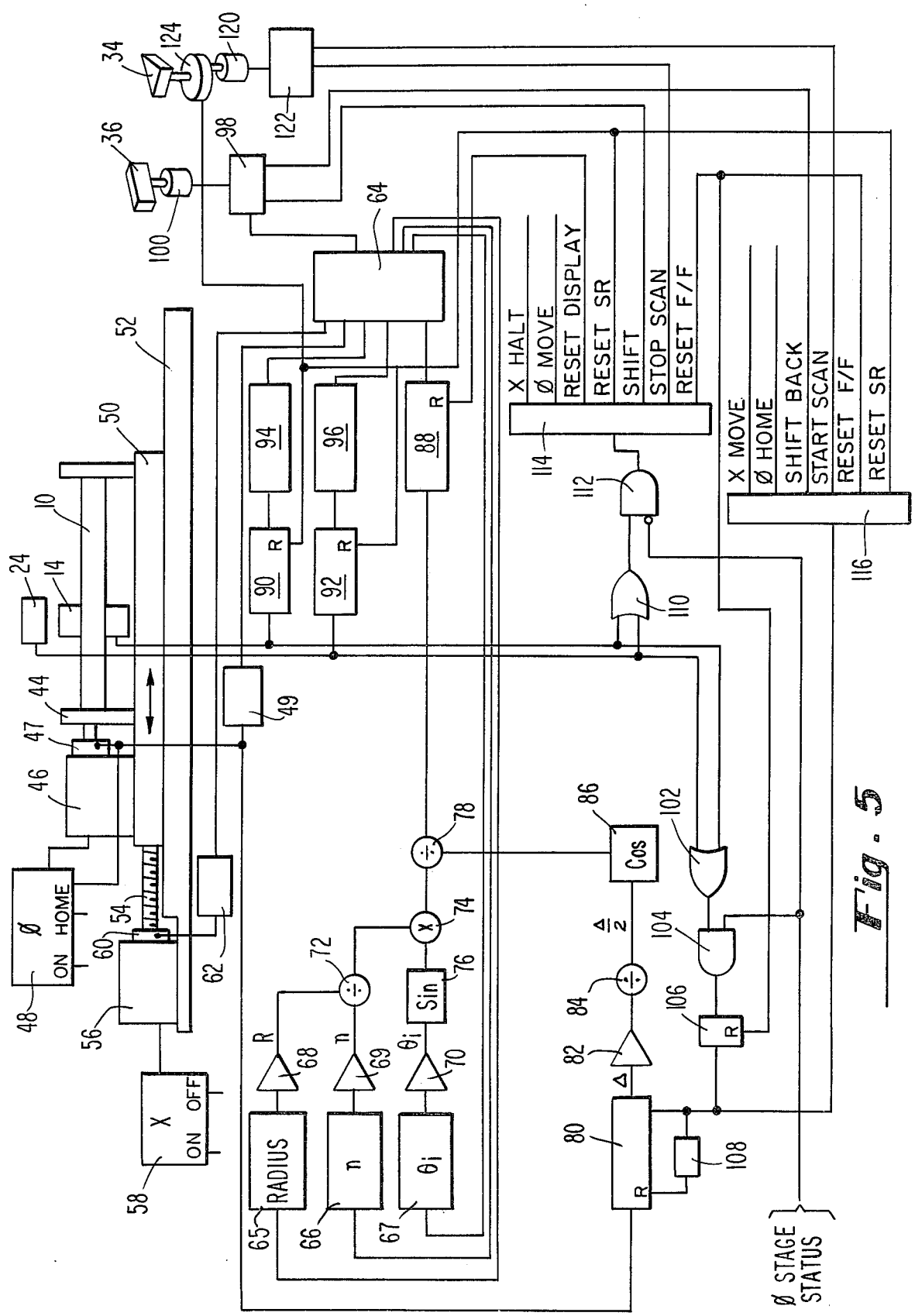
FIG. 5 is a schematic diagram of a control system for practicing the invention.

Turning now to FIG. 5, a presently preferred embodiment of a system for carrying out the above-described inspection procedure is shown. Blank 10 is chucked in a mounting fixture 44, which is in turn rotated by a rotary or $\phi$ stage including a motor 46 operated by motor control 48. Resolver 47 is coupled to the blank for outputting signals reflecting the angular position of the blank. The blank rotating and chucking system is carried by a carriage 50 slidably mounted upon ways 52 and driven by a lead screw 54 or the like. The lead screw is rotated by means of an appropriate driver motor 56, operated by a controller 58. Another resolver 60 produces signals which represent the angular rotation of lead screw 54, and therefore the degree of axial translation of the blank. The latter signals are applied to an X position display and decode unit 62, and also if desired to a digital computer 64. While the latter is not necessary to the practice of the invention, it has been found that a computer is highly useful logging and recording process data generated by the system, and for rapidly controlling the system. In like manner, signals from resolver 47 are applied to computer 64 and also to a decoding and display state 49.

A plurality of setpoint generators 65, 66 and 67 are provided for supplying signals representing the radius R of blank 10, the index of refraction n of the blank material, and the incident angle $\theta_i$ of the inspection beam, respectively. These signals may be provided by means of thumb wheels or other manually adjustable units, or may be provided by computer 64 in accordance with data entered into the computer. Such data may, for example, reflect measurements made of the blank preparatory to the scanning procedure. Other information such as curvature or bow of the blank may also be entered into the computer so that a proper Y translation of the inspection beam can be selected in accordance with the axial inspection position and angular orientation of the blank.

Signals provided by generators 65, 66 and 67 are passed through digital-to-analog converters (hereinafter d/a converters) 68, 69 and 70 respectively. The signals representing radius R and index of refraction n are divided in an appropriate signal divider 72, and applied to a signal multiplier 74. A sine signal generator 76 outputs a signal representing the sine of the angle of incidence $\theta_i$ to the multiplier stage, so that the output of stage 74 comprises an analog of the quantity $$R \sin \theta_i$$

This quantity is then applied to another dividing stage 78.

A signal from resolver 47 and representing the angular position of the blank is supplied to a counter 80, which produces an output signal which is converted by d/a converter 82 and divided by a factor of two in divider stage 84. The resulting signal is processed through a cosine generator 86 and supplied to divider stage 78 to obtain a signal representing the quantity $$\frac{\frac{R}{n} \sin \theta_i}{\cos \frac{\Delta}{2}}$$

This quantity is supplied to a peak signal hold-and-display unit 88 which displays and/or records information representing the radius at which a sensed inclusion is located. If it is desired to fully automate the system, the information representing radius r is also applied to computer 64 wherein the data is logged for future use and analysis.

Signals outputted by solid inclusion detector 14 are applied to a first shift register 90. In like manner outputs from void inclusion detector 24 are applied to a similar shift register 92. The shift registers are connected in conventional fashion to in effect disregard the first two signal pulses applied thereto, outputting a signal when a third pulse arises. This is necessitated by extraneous pulses which arise as the inspection beam is scanned past either side of the blank. The reset terminals of the shift registers are coupled to the scanning mechanism, to be reset after each scan; and also to another portion of the system for resetting after the rotational inspection step. The third-pulse outputs are applied from shift registers 90 and 92 and counters 94 and 96, respectively. In an automated embodiment the counted signals may also be applied to computer 64 to be entered into the data logging section of the computer for future reference and analysis. Computer 64 produces an output coupled to a motor control 98 for operating a positioning servo 100 so as to orient parallelogram prism 36 at an appropriate angle for displacing the inspection beam. The amount of beam displacement is determined from data previously gathered relating to the radius and the bow, if any, of blank 10; and from signals representing the angular and axial position of the blank.

Signals from inclusion detectors 14 and 24 are also applied to a first OR gate 102, the output of which is coupled to an AND gate 104, as shown. Another input to AND gate 104 is derived from an appropriate transducer and indicates whether the rotating or $\phi$ stage is operational. If enabled, AND gate 104 triggers flip-flop 106, whose input is coupled to an on/off terminal of counter 80. The flip-flop is inhibited during the transverse scanning process, and is enabled only when blank 10 is rotated. The signal also triggers a time delay 108 which resets counter 80 after some predetermined period of time has expired.

Signals from the void and solid inclusion detectors are further applied to a second OR gate 110, and thence to an input terminal of a second AND gate 112. The $\phi$ state status signal is also applied to the AND gate through an inverting terminal, and the AND gate output coupled to a one-shot switch bank 114. Outputs of the one-shot are fed back to appropriate points in the control system, as are outputs from a second bank 116 which is responsive to the state of flip-flop 106.

The first bank of one-shot stages or switches 114 is coupled to AND gate 112 and responsive thereto to output signals to various points in the control system in order to cause the system to cease operating in the transverse scanning mode and to commence rotational scanning. In like manner one-shot switch bank 116 is activated by flip-flop 106 to cause the system to reenter the transverse scanning mode. Finally, a motor 120 operated by motor controller 122 drives prism 34 through an oscillatory drive train 124.

The operation of the system of FIG. 5 will now be described in detail, making specific reference to the enumerated elements therein, and occasional reference to features of FIGS. 1-4. When the system is initially energized carriage 50 is in one extreme position, and drive motor 56 energized for moving blank 10 axially in front of detectors 14, 24. The rotational or $\phi$ stage is locked in a predetermined "home" position so that blank 10 is not rotating; similarly, parallelogram prism 36 is in a "home" position whereby it extends perpendicular to the path of the inspection beam. Prism drive motor 120 is energized by an appropriate motor controller 122 and, through an appropriate mechanism 124, causes prism 34 to oscillate back and forth. In this manner the inspection beam 12 may be caused to translate across blank 10 perpendicularly to the axis thereof. After each translation motor 56 is energized by controller 58 to advance the blank by some small increment and thus update counter 62.

Consider now that an inclusion, either solid or void, is detected. A signal is produced by one of detectors 14, 24 depending upon the nature of the inclusion. Inasmuch as the system responds in the same fashion regardless of the type of inclusion, for purposes of description it will be assumed that a solid inclusion is detected and accordingly a signal outputted by detector 14.

The signal from detector 14 is applied to a shift register 90 which is connected in conventional fashion so as to in effect disregard the first two pulses applied thereto, but output a signal upon the arising of a third pulse. Accordingly, the first two pulses increment the register but do not cause it to produce a signal, and the third pulse is counted. The output of detector 14 is also applied to OR gates 102 and 110. Inasmuch as the $\phi$ stage is inoperative there is no signal therefrom, and AND gate 104 remains disabled despite the production of a signal by OR gate 102. Second OR gate 112, by virtue of its inverting input, is activated by the detector signal in the absence of activity by the rotational or $\phi$ stage. Switch bank 114 responds to the output of the AND gate to produce a number of command signals to discontinue the transverse scanning operation, and institutes a chordal scanning procedure for identifying the position of the detected inclusion. Signals from switch bank 114 are applied to the "off" terminal of motor control 58 to halt axial translation of the system. Another signal is applied to motor control 48 so that blank 10 begins to rotate. Display 88 is reset as are shift registers 90 and 92.

Switch bank 114 also operates controller 98 to cause servo 100 to rotate the parallelogram prism 36 by a predetermined amount. The beam scanning system which operates prism 34 is also halted, and the prism disposed in a central or "home" position. The slight offset of the parallelogram prism now deflects the beam some distance Y from its nominal path so that it impinges upon the surface of blank 10 at the desired angle of incidence $\theta_i$. Finally, flip-flop 106 is reset.

With the inspection beam offset so as to effect a chordal scan, as illustrated in FIG. 3, and blank 10 rotating the already-detected inclusion will eventually encounter the scanning beam. One of the detectors then produces a signal which is transmitted through both OR gates 102 and 110 to AND gates 104 and 112, respectively. Due to the fact that the $\phi$ stage is in operation the second AND gate 112 remains inhibited, and first AND gate 104 is enabled. The latter triggers flip-flop 106 to start angle counter 80. The latter accumulates signals from resolver 47 which represent the angular rotation of the blank. When a second pulse occurs, indicating that the inclusion has once again crossed the inspection beam bath, the counter is stopped and the count which it has accrued may be taken to represent the total included angle $\Delta$ lying between radii extending from the center of the blank to the points at which the inclusion traversed the chordal inspection beam. The digital angle signal is converted to an analog function by d/a converter 82 and divided by a factor of 2 in dividing stage 84. The half-angle value is then operated upon by cosine generator 86 to achieve the function $\cos \Delta/2$.

At the same time signals representing the radius R of blank 10, the index of refraction n, and the incident angle $\theta_i$ are converted to analog form by d/a converters 68, 69 and 70, and the quotient R/n obtained in dividing stage 72 and applied to a multiplier 74. At the latter stage, the quantity R/n is multiplied by sine $\theta_i$ and the resulting quantity passed to dividing stage 78. The output of the latter comprises a signal in accordance with expression (7) and which represents the radius r at which the inclusion lies. This signal is applied to peak hold display 88. As is familiar to those skilled in the art a peak hold unit displays the value of a peak or local maximum in a signal, and thus is not responsive to interim signals but only to those maxima which represent the desired status.

In addition to stopping counter 80, the second pulse outputted by detector 14 causes flip-flop 106 to change state once more, actuating one-shot switching bank 116. Accordingly, the motor controller 48 causes the motor to drive blank 10 "home" to a predetermined angular position. Controller 58 is again energized so that motor 56 causes carriage 50 to translate, and controller 98 operates servo 100 to cause parallelogram prism 36 to return to its normal position transverse to the scanning beam. The scanning of the beam is re-started by a signal to controller 122, and flip-flop 106 is reset. Finally, shift registers 90 and 92 are also reset.

In order to monitor the process and to determine the precise location of the blank 10 both axially and radially the outputs of displays 62 and 49 may be recorded. The value of display 62 reflects the axial positioning of the blank, while the information of display 49 indicates the rotational position thereof. Counter 94 and 96 log the number of inclusions which have been detected, and display 88 sequentially indicates the radius of each detected inclusion. For some applications, particularly those carried on at low production rates the data from displays and/or counters 62, 49, 94, 96 and 88 can be manually logged and the number of inclusions and their locations noted so that the acceptability of the blank can be determined. Alternatively, the information may be logged in a digital computer 64. The latter approach has the advantage of allowing additional calculations to be made rapidly, such as the relative density of inclusions in any given portion of the blank. Use of computer 64 further serves to accelerate the speed at which the inspection process can be carried on inasmuch as it can rapidly and automatically adjust the process parameters such as radius, index of refraction and angle of beam incidence, and determine the appropriate offset Y for the inspection beam at any point along a lowed blank.

It will now be appreciated that there has been disclosed herein an improved inspection system for discovering, identifying and locating various types of inclusions within a blank of material. The system may be used with blanks which are not optically transparent; and lends itself readily to automation and thus to high-volume usage in commercial applications. It will also be evident from the foregoing description that certain aspects of the invention are not limited to the particular details of the examples illustrated, and it is therefore contemplated that other modifications or applications will occur to those skilled in the art. It is accordingly intended that the appended claims shall cover all such modifications and applications as do not depart from the true spirit and scope of the invention.

What is claimed as new and desired to be secured by Letters Patent of the United States is:

1. An inspection system for detecting inclusions in a generally cylindrical member, comprising:
    a source for producing a beam of electromagnetic radiation of a wavelength to which the member is substantially transparent;
    mounting means for rotatably disposing the member in the path of said beam, the longitudinal axis of the member being displaced from said beam to cause said beam to traverse a chord of the cylindrical member;
    sensor means disposed in proximate relation to said mounting means for receiving at least a portion of said beam exiting from the member; and
    signal processing means responsive to the sequential interruption of said beam for determining the position of an inclusion in the member.

2. A system according to claim 1, wherein said sensor means comprises a first photo sensor positioned to receive scattered portions of said beam upon deflection of said beam from undisturbed transmission through the member by a void inclusion.

3. An inspection system according to claim 2, further including transducer means coupled to said mounting means for outputting a signal representing the angular disposition of the member, said signal processing system being responsive to the output of said transducer and to said photosensor means to produce an indication of the location of detected inclusions in the member.

4. An inspection system according to claim 3, wherein said radiation source comprises a laser.

5. An inspection system according to claim 4, further including a prism disposed in the path of the beam outputted by said laser for offsetting said beam by some distance Y from a beam path extending through the contour of the member.

6. An inspection system for detecting void and opaque inclusions in a generally cylindrical member, comprising:
   a light source producing a beam of light of a wavelength to which the member is substantially transparent;
   mounting means for disposing said cylinder in the path of said light beam so that the beam traverses the cylinder along a path defining a chord of the cross-sectional area of the member;
   sensor means for receiving at least portions of said light beam issuing from the member;
   first means for effecting axial translation of the member with respect to said light beam;
   second means for effecting rotation of the member with respect to the light beam;
   first signal processing means coupled to said first means and to said sensor means and responsive to signals from said sensor means to cause axial translation to cease and rotation of the member to commence; and
   second signal processing means coupled to said sensor means and responsive to changes in said light beam for outputting signals indicating the position of inclusions within the member.

7. An inspection system according to claim 6, wherein said sensor means comprises a first photosensor positioned to receive light issuing from said member after scattering thereof by a void inclusion.

8. An inspection system according to claim 7, wherein said sensor means further includes a second photosensor disposed adjacent said member to receive said light beam after undisturbed passage through said member.

9. The method of locating inclusions in a rotatable member, comprising the steps of:
   directing a light beam transversely through the member at a location spaced from the axis thereof;
   rotating the member with respect to the light beam to cause the beam to intercept the same inclusion twice in succession;
   determnining the rotation of the member required to effect a second interruption of the light beam; and
   determining the location of the inclusion in a plane of the member.

10. The method of locating inclusions in a rotatable member, comprising the steps of:
    providing a beam of electromagnetic radiation at a wavelength to which the member is substantially transparent;
    scanning said beam transversely across the member at successive locations along the axis of rotation thereof;
    detecting an interruption of said beam by an inclusion disposed in a given plane in the member;
    thereafter fixedly positioning said beam and rotating the member, said beam traversing the member in said given plane and at some distance from the axis of rotation thereof;
    detecting an interruption of the beam by an inclusion in the member; and
    determining the rotation of the member required to effect a subsequent interruption of the beam;
    whereby the location of the inclusion in said given plane may be determined.

11. The method according to claim 10 wherein interruptions of said beam by a void inclusion are detected by sensing light scattered thereby.

12. The method according to claim 11, further including the step of detecting solid inclusion by sensing a diminution in the light which traverses the member.

13. The method according to claim 12 wherein the member is a substantially cylindrical glass element.

* * * * *